United States Patent [19]

Heim et al.

[11] 4,009,188
[45] Feb. 22, 1977

[54] CONTINUOUS PROCESS FOR RECOVERY OF GLYCIDE

[75] Inventors: Wolfgang Heim, Bruchköbel; Axel Kleemann, Hanau; Heinz Kolb, Hanau; Gerd Schreyer, Hanau, all of Germany

[73] Assignee: Deutsche Gold- und Silber-Scheideanstalt vormals Roessler, Frankfurt, Germany

[22] Filed: Feb. 19, 1975

[21] Appl. No.: 551,015

[30] Foreign Application Priority Data

Feb. 25, 1974 Germany .......................... 2408948

[52] U.S. Cl. .................. 260/348.5 L; 203/72; 203/73; 203/80; 203/89
[51] Int. Cl.² .................. C07D 301/12; B01D 3/10; B01D 3/28
[58] Field of Search .................. 203/72, 73, 74, 77, 203/80, 81, 89; 260/348 R, 348.5 L

[56] References Cited
UNITED STATES PATENTS

| 3,122,569 | 2/1964 | Kaman | 260/348.5 L |
| 3,156,709 | 11/1964 | Allan | 260/348.5 L |
| 3,374,153 | 3/1968 | Naglieri | 260/348.5 L |
| 3,392,091 | 7/1968 | Hohenschutz | 203/73 |
| 3,509,183 | 4/1970 | Wenzke et al. | 260/348.5 L |
| 3,655,524 | 4/1972 | Mednick | 260/348.5 L |

Primary Examiner—Wilbur L. Bascomb, Jr.
Attorney, Agent, or Firm—Cushman, Darby & Cushman

[57] ABSTRACT

Glycide is prepared by reacting allyl alcohol with hydrogen peroxide in the presence of a tungsten compound as a catalysts the excess allyl alcohol and the greatest part of the water distilled off, the sump mixture obtained in the distillation is split at 110°–220° C. and 5 to 60 torr in a thin layer evaporator into a volatile portion which is predominantly glycide, high boiling by products and the residual part of the water and a sump portion of glycerine, polyglycerine and catalysts. The volatile liquid portion is broken into glycide, water and high boiling byproducts at 5 to 60 torr in a distillation apparatus directly connected to the thin layer evaporator.

3 Claims, 1 Drawing Figure

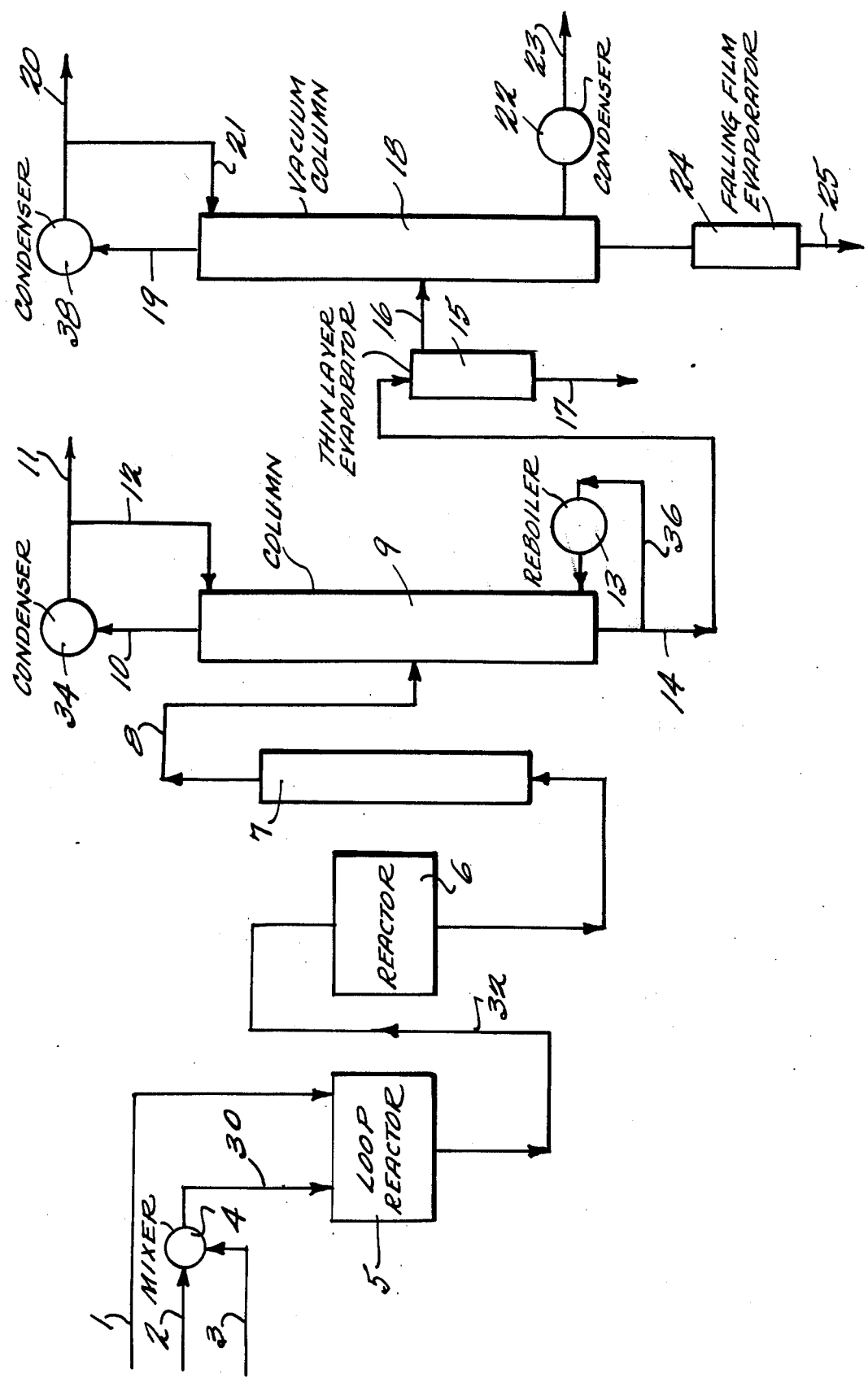

CONTINUOUS PROCESS FOR RECOVERY OF GLYCIDE

It has been known for a relatively long time that glycide can be produced by epoxidation of allyl alcohol with active oxygen containing compounds. Thus, for example, organic percarboxylic acids have been called upon for this purpose, especially peracetic acid which is readily available commercially (see Phillips German Pat. No. 1,019,307, Fisher German Offenlegungsschrift No. 1,618,336 and Wenzke German Offenlegungsschrift No. 1,768,953). Performic acid has also been recommended for the epoxidation of allyl alcohol (see LaPorte French Pat. No. 1,519,147).

Although in all of these processes the epoxidation reaction itself leads to the glycide containing reaction mixture with relatively good yields and favorable reaction speeds without the need to use catalysts they have a serious disadvantage.

From the percarboxylic acid there is formed the corresponding carboxylic acids which can react relatively easily with the glycide formed during the course of working up the product and therewith are responsible for a considerable reduction in yield of pure high percentage glycide.

In still stronger measure the fact that it was previously not possible to obtain a high percentage glycide completely free of acids prevents the industrial use of such a process.

Even the presence of traces of acids in the high percentage glycide lowers the stability of this substantially. It has been observed that a 98% glycide having 0.2 weight % acetic acid impurity after storing for 8 days at room temperature only has a glycide content of 85–88%.

Even storing at 0° C. reduces the content in the same time span to 92–93%. On the contrary in storing a glycide completely free of acid at room temperature there is only a reduction of glycide content of about 2% per month or 0.5% in 8 days. From this it can be seen that a glycide containing only small amounts of acid is very unstable and therewith cannot be considered as an industrial product. The epoxidation with peracids was likewise industrially impracticable.

However, processes which avoid peracids also have definite disadvantages.

It is known to epoxidize allyl alcohol with alkyl or aralkyl hydroperoxides in the presence of heavy metal catalysts, as for example, vanadium or molybdenum compounds (see German Offenlegungsschrift No. 1,543,026, Institute French Pat. No. 1,505,332, German Offenlegungsschrift No. 1,643,610, Progil French Pat. No. 1,539,209, Progil French Pat. No. 1,548,678, Kollar U.S. Pat. No. 3,625,981, Hayden German Offenlegungsschrift No. 2,037,703, Vangermain German Offenlegungsschrift No. 1,518,644 and Wattimena German Offenlegungsschrift No. 2,015,542).

In these processes there result relatively long reaction times and practically no quantitative hydroperoxide conversion. Conditioned by the last fact the hydroperoxide still present in the reaction mixture must be destroyed before the true working up. Through this there results a relatively expensive working up of the reaction mixture. Since the reaction generally requires the presence of as inert a solvent as possible, for isolation of a pure glycide there must be carried out expensive separatory processes.

Additional difficulties are caused by the fact that the alcohols formed from the hydroperoxide must be recycled again to recover hydroperoxides. This is generally effected by dehydration of the alcohols to the corresponding olefins hydrogenating to the saturated hydrocarbons and heating the latter with oxygen. Furthermore the relatively expensive catalysts must be recovered.

There have also been known for a long time other methods for the production of glycide by epoxidation of allyl alcohol using hydrogen peroxide in the presence of catalytic amounts of acid or neutral salts of tungstic acid. These reactions were likewise the subject of numerous patents, see for example Carlson U.S. Pat. No. 2,833,787, Skinner U.S. Pat. No. 2,833,788, Kaman German Auslegeschrift No. 1,144,276, Graham U.S. Pat. No. 3,156,709 and Markina German Offenlegungsschrift No. 1,816,060. (The entire disclosures of the United States patents mentioned in this paragraph are hereby incorporated by reference and relied upon). The reaction is carried out in dilute aqueous medium at a pH of 3 to 8 and at temperatures of 30° to 70° C. in the presence of excess allyl alcohol. After complete reaction of the hydrogen peroxide the yield of glycide in the reaction mixture under optimune reaction conditions can be about 80% of theory.

However, until now these relatively simple process variants have not been employed to produce glycide on an industrial scale. The basis for this is that as yet no suitable process for the separation of the reaction mixture or isolation of pure high percentage glycide without large loss of yield has been available. Here also the relatively expensive catalyst as well as the allyl alcohol added in excess have to be recovered. Furthermore the water and glycide secondary products must be separated from the glycide itself.

Attempts to remove the tungsten catalyst from the reaction mixture with the help of ion exchangers were not successful; apart from the fact that the quantitative recovery of the catalyst is carried out only with a proportionate very large excess of ion exchanger, also because of polycondensation of the glycide to polyglycerine there is considerable lowering of the yield. A further difficulty is that in this type of catalyst recovery the ion exchangers based on polystyrene previously used commercially swell irreversibly and after several applications become unusable.

It has also been proposed to catalyze the epoxidation by use of anion exchangers loaded with tungstic acid, see U.S. Pat. No. 3,156,709. In the reworking of this process, however, it has been proven that there cannot be avoided the dissolving of the tungstic acid from the ion exchanger so long as there is not kept a constant pH of 5–6. However, at such a pH value the reaction is so strongly retarded that unusably long reaction times result and furthermore a considerable part of the hydrogen peroxide is decomposed.

Furthermore there has been recommended the use of neutral calcium tungstate as catalyst, see Markina German Offenlegungsschrift No. 1,816,060. This procedure also involves relatively long reaction times and hydrogen peroxide losses. Additionally the difficultly soluble neutral calcium tungstate does not precipitate quantitatively immediately after the reaction but instead there is required an addition of more calcium ions.

The isolation of the glycide from the reaction mixtures according to the previous state of the art was carried out in the following manner:

The excess allyl alcohol was recovered by distillation in a vacuum up to 150 torr in the form of an aqueous solution, if the residence time for the glycide containing aqueous solution in the sump of the distillation column was sufficiently short, i.e. up to 60 minutes, there resulted no large loss of the glycide by hydrolysis. The mixture still containing water, glycide, higher boiling secondary products and the catalyst could be separated by way of a thin layer evaporator or another evaporator of suitable construction with correspondingly short residence time, namely to a water and glycide containing distillate and a sump product containing glycerine, higher boiling byproducts and the catalyst. However, the last named distillate must still be fractionated in a vacuum to recover a pure high percentage glycide. Thus glycide is twice distilled in the presence of water. Conditional upon the large heat of evaporation of the water there results thereby an uneconomically high expenditure of energy. Besides there occurs a considerable loss of glycide because of the hydrolysis.

In the processes according to the state of the art the following disadvantages must be considered:

1. High expenditure of energy, which is also industrially disadvantageous.
2. Relatively high lost of yield in the course of the isolation of the pure glycide.
3. Difficulties in the recovery of tungsten containing catalysts because of the relatively large amounts of high boiling and viscous condensation products of glycide.

In contrast it has now been found that by avoiding the double condensation and reheating of glycide and water the yield of glycide is increased substantially, the expenditure of energy decreased and at the same time the catalyst is easily recovered in the reaction of allyl alcohol with hydrogen peroxide in the presence of tungsten compounds as catalysts if the sump mixture obtained in known manner after distillation off of the excess allyl alcohol and the greatest part of the water under vacuum likewise in known manner is split at 110L to 220L C. and 5 to 60 torr in a thin layer evaporator into a volatile liquid portion which is predominantly glycide, high boiling byproducts and the residual portion of the water and a sump portion of glycerin, polyglycerine and catalyst. The volatile liquid portion is broken into glycide, water and high boiling byproducts at a pressure of 5 – 60 torr in apparatus, e.g. distillation apparatus directly connected to the thin layer evaporator.

The preferred pressure is 10–30 torr. Preferably the separation of evaporated liquids takes place in a column.

By direct splitting of the hot evaporated liquid, i.e., the vapor mixture of glycide, high boiling byproducts and residual water the condensation and reheating of the glycide containing mixture is avoided and therewith both energy saved and the hydrolysis stopped by the substantially shorter time of contact of glycide and water in this process step.

The glycide taken off above the sump of the column is very pure, at least 99% and is obtained in a yield of 76% and more based on the added hydrogen peroxide.

The process steps up to the direct separation of the evaporated liquid is carried out in known manner, see for example, Levine German Offenlegungsschrift No. 2,252,938.

As stated above until now considerable loss of yield of glycide occurred because of hydrolysis. This may be the reason why previously in the literature there cannot be found any information as to the yield of isolated pure glycide.

As thin layer evaporators there can be used apparatuses of known construction, for example rotor evaporators with fixed as well as the movable wiper blades as well as centrifugal evaporators as shown for example in Vauch-Muller "Grundoperationen chemischer Verfahrenstechnik, 1966." The recovery of the catalyst containing sump (or bottoms) in the last step can take place in known manner.

There can be employed any of the known tungsten containing catalyst, such as those set forth in the art mentioned above for example. Thus there can be used tungstic acid, calcium tungstate, sodium tungstate, potassium tungstate, sodium acid tungstate, potassium acid tungstate, tungsten -8- hydroxyquinoline complex, hydrogen tungstate, salt of amberlite IRA-400 (quaternary ammonium resin)

Unless otherwise indicated all parts and percentages are by weight.

The invention will be understood best in connection with the drawings wherein the single FIGURE is a diagrammatic illustration of the process.

Referring more specifically to the drawings.

Aqueous allyl alcohol is fed into the loop reactor 5 via line 1. Simultaneously via line 2 aqueous hydrogen peroxide and via line 3 aqueous solution of tungsten containing catalyst were intensively mixed in a static mixer 4 and likewise led via line 30 to the reactor 5. The loop reactor 5 is equipped with a heating or cooling apparatus to maintain a constant temperature. For completion of the reaction (quantitative reaction of the hydrogen peroxide) the reaction mixture goes via line 32 to reactor 6 and also optionally through residence space 7. The reacted homogeneous reaction solution contains glycide, water, excess allyl alcohol, secondary products from glycide, as for example glycerine and polyglycerine, as well as traces of acrolein and the catalyst and is fed into vacuum column 9 via line 8. There is drawn off as distillate via line 11 after condensation in condenser 34 of the vapors leaving the column 9 via line 10, allyl alcohol and a portion of the water. To install the necessary reflux ratio a portion of the distillate is returned via line 12 to the top of the column. The heating of the column sump takes place through the reboiler 13 which for example can be built in the form of a falling film evaporator. This has the advantage that the sump product is only exposed to the heat for a relatively short period of time and the hydrolysis of glycide to glycerine cannot occur in a mentionable amount. In principle, however, all possible types of evaporators can be used for this purpose. It can be seen from the drawings that a portion of the product leaving the sump via line 14 is diverted through line 36 through reboiler 13 and returned to the column 9.

The pressure at the top of column 9 should be in the range of 20 – 200 torr, preferably between 80 and 130 torr. The distillation conditions are so regulated that the sump product drawn off via line 14 has a glycide content of 30 – 60 weight %, preferably 40–50 weight %.

This glycide concentrate is now brought into the thin layer evaporator 15 whose volatiles line 16 is directly connected with the vacuum distillation column 18. As residue from evaporator 15 there is drawn off via line 17 a highly viscous mixture of glycerine, polyglycerine and, in a given case, other high boiling condensation products of glycide as well as the entire catalyst. A vapor mixture of glycide and water as well as traces of glycerine passes via line 16 to the vacuum column 18. The separation of these components takes place in column 18 which is operated in a pressure range of 5–60 torr, preferably 10–30 torr and likewise has a thin layer or falling film evaporator 24 as a reboiler. The vapor leaving the column via line 19 is condensed in condenser 38 and is drawn off via line 20 as distillate.

A portion of the distillate is returned to the top of the column via line 21 to maintain the desired reflux ratio. Pure high percentage glycide is condensed in condenser 22 and by way of a temperature regulated valve is drawn off sidewise above the lower end of column 18 through line 23. The higher boiling products which essentially consist of glycerine and polyglycerine were removed from the sump via line 25.

The product drawn off via line 17 contains the catalyst in enriched form (about 20–60 weight %), which is very well suited for a practically lost-free recovery. From the product drawn off via line 25, which contains 50 to 80 % glycerine, there can be recovered a very pure glycerine through a further fractionation in vacuum. The distillate drawn off via line 20 practically consists of only water. It contains only traces of glycide. Accordingly without further treatment it is suited for reuse in the reaction step, for example to dilute the allyl alcohol or catalyst solution.

In light of the preceeding description the advantages of the process of the invention become clear. It is possible therewith not only to isolate the glycide in higher purity and yield but also correspondingly to recover the glycerine formed as byproducts as well as the catalyst in a form very well suited for further preparations.

Further explanation of the invention is given in the following example:

EXAMPLE

The experiment was carried out for an evaluation time of 370 hours in a continuous laboratory apparatus, which was layed out for a throughput of 3 moles per hour.

The apparatus corresponded in the essential parts to the arrangement in the drawing with the exception that the catalyst solution was already premixed with the aqueous hydrogen peroxide solution.

Starting Solution I 15.0 Grams of tungstic acid were mixed with 59.0 ml of 1 N NaOH solution and 100 ml of water and dissolved hot with stirring, after cooling to room temperature stirred in to an about 30% hydrogen peroxide solution containing exactly 10.0 moles of hydrogen peroxide and filled up with water to 2,000 ml.

Starting Solution II

510 Grams (equal 8.89 moles) of allyl alcohol (>99%) were filled up with water to 1,000 ml.

Both solutions were fed into a loop reactor by means of a pump in fixed amounts (on the average hourly 597 ml of solution I, corresponding to 2,985 moles of hydrogen peroxide and 913 ml of solution II). The reaction was carried out in known manner. The reaction temperature was held constant at 40° C. The hydrogen peroxide reaction was >99%. The reaction yield of glycide based on the hydrogen peroxide amount to about 81% of theory.

The reaction mixture was brought into the middle of a 2 meter high packed column having a nominal width of 50 mm and operated on a top pressure of 130 Torr. As evaporator there was used a thin layer evaporator (Samboy L 50 of V4A steel). At a reflux ratio of about 1 and a head (top) temperature of 51° C. there was drawn off a distillate averaging 27 weight % of aqueous allyl alcohol and an allyl alcohol free sump product was obtained having on the average the following composition:

glycide 43.18 weight %
glycerine 4.12 weight %

The content of glycide in the distillate was under 0.1%. The calculated glycide yield up to this step on the averaged amounted to 77.5% of Theory based on the hydrogen peroxide. This sump mixture (crude glycide concentrate) was fed with the help of a hermatically sealed pump into the thin layer evaporator 15 jacked heated to 210–212° C. As residue there was discharged from here a highly viscous brown mass which contained about 15 weight % glycerine and about 25 weight % tungstic acid as the sodium acid salt. The volatiles in the distillation pass by way of well insulated line 16 (see the drawing) into column 18, between the second and third column section, which is operated at a head (top) pressure of 19 torr. The column 18 consists of three column sections with the following dimensions:

Section 1: 800 mm long; nominal width 40 mm, V4A steel gauze rings 6 mm as packing.
Section 2: 1900 mm long; nominal width 40 mm; glass Raschig rings 6 mm as packing.
Section 3: 1500 mm long; nominal width 40 mm; glass Raschig rings 6mm as packing.

Overhead there was drawn off an aqueous distillate with an average of <1.0 % glycide. Pure >99% glycide was drawn off over a temperature controlled steam valve between the first and second sections.

As evaporator 24 there was employed a further thin layer evaporator (QVF, heating surface 0.016 m²), which was jacked heated to 190° C. Via line 25 (see the drawing) there was discharged a nearly colorless product which contained on the average 61% glycerine and 8% glycide.

The following temperature profile was established in distillation column 18

Glycide take off 78° C.
Feed place (inflow of volatiles from evaporator 15) 90° C.
Top of column 23° C.

Per hour there were obtained on the average 167 grams of a product containing 99.3% of glycide, corresponding to 2.17 moles via line 23. This corresponds to a pure yield of 76.4% of theory based on the hydrogen peroxide.

The glycide yield based on the allyl alcohol was about 3% higher.

From evaporator 15 via line 17 there was drawn off the catalyst containing sump; the tungsten catalyst after dilution of the sump with water was recovered by passing over a basic ion exchanger according to known process such as that set forth in the art cited above.

We claim:
1. In a process for preparing glycide by reacting allyl alcohol with aqueous hydrogen peroxide employing a tungsten compound as a catalyst, (1) distilling off from the reaction mixture produced excess alcohol and the predominate part of the water, then taking the sump mixture from said distillation and (2) distilling it at 110°–220° C. and 5 and 60 torr into a volatile portion which is predominantly glycide, high boiling byproducts and the residual part of the water and a sump portion of glycerine, polyglycerine and catalyst, the improvement comprising taking said volatile portion and immediately after said distillation at 110°–220° C., before the volatile portion has cooled substantially, separating said volatile portion at 5 to 60 torr by distilling off the water in a column having a sump, recovering glycide by drawing it off at a point above the sump of said column and removing the high boiling byproducts from the sump.

2. A process according to claim 1 wherein there is employed for preparing glycide a starting mixture consisting essentially of allyl alcohol, water, hydrogen peroxide and catalyst.

3. The process of claim 1 comprising carrying out said distillation of said volatile portion at 10–30 torr.

* * * * *